United States Patent
Ley et al.

(10) Patent No.: US 7,476,750 B2
(45) Date of Patent: Jan. 13, 2009

(54) METHOD FOR SYNTHESIZING COMPOUND AND CATALYST FOR SYNTHESIS REACTION

(75) Inventors: Steven V. Ley, Cambridgeshire (GB); Martin D. Smith, Cambridgeshire (GB); Sophie Lohmann, Cambridgeshire (GB); Steven P. Andrews, Cambridgeshire (GB); J. Paul Attfield, Central Scotland (GB); Hirohisa Tanaka, Shiga (JP); Kimiyoshi Kaneko, Kanagawa (JP)

(73) Assignees: Cambridge University Technical Services Limited, Cambridge (GB); Daihatsu Motor Co., Ltd., Osaka (JP); Hokko Chemical Idustry Co., Ltd., Tokyo (JP)

( * ) Notice: Subject to any disclaimer, the term of this patent is extended or adjusted under 35 U.S.C. 154(b) by 0 days.

(21) Appl. No.: 11/587,340

(22) PCT Filed: Apr. 25, 2006

(86) PCT No.: PCT/JP2005/008317

§ 371 (c)(1), (2), (4) Date: Oct. 24, 2006

(87) PCT Pub. No.: WO2005/105719

PCT Pub. Date: Nov. 10, 2005

(65) Prior Publication Data

US 2007/0167632 A1    Jul. 19, 2007

(30) Foreign Application Priority Data

Apr. 28, 2004 (JP) .............................. 2004-132553

(51) Int. Cl.
*C07F 17/02* (2006.01)
*C07C 5/08* (2006.01)

(52) U.S. Cl. ...................................... 556/136; 585/320
(58) Field of Classification Search ................. 585/310, 585/320, 535; 502/302, 303, 525; 556/136, 556/466; 549/80; 365/151; 564/484; 570/193
See application file for complete search history.

(56) References Cited

U.S. PATENT DOCUMENTS

| | | | |
|---|---|---|---|
| 5,210,211 A | 5/1993 | Hodges et al. | |
| 5,389,659 A | 2/1995 | Ross et al. | |
| 2003/0171625 A1 | 9/2003 | Ishii et al. | |
| 2006/0106261 A1 | 5/2006 | Ishii et al. | |

FOREIGN PATENT DOCUMENTS

| | | |
|---|---|---|
| EP | 0 854 849 B1 | 10/2001 |
| JP | H06-25175 | 2/1994 |
| JP | H06-508370 | 9/1994 |
| JP | H10-114691 | 5/1998 |
| JP | H11-512430 | 10/1999 |
| JP | 2001-342176 | 12/2001 |
| JP | 2003-327547 | 11/2003 |
| WO | WO 97/10193 | 3/1997 |

OTHER PUBLICATIONS

Mio, M.J., et al., One-Pot Synthesis of Symmetrical and Unsymmetrical Cisarylethynes by a Modificationof the Sonogashira Coupling Reaction, Aug. 30, 2002, Organic Letters, vol. 4, No. 19, pp. 3199-3202.*

Norio Miyaura et al., "Palladium-Catalyzed Cross-Coupling Reactions of Organboron Compounds", Chemical Reviews, 1995, 95(7), 2457-2483.

Antonia F. Stepan, "Palladium-Containing Perovskites as New Catalysts for Cross Coupling Reactions", Pembroke College, 2004, p. ii-55.

Martin D. Smith et al., "Palladium-containing perovskites: recoverable and reuseable catalysts for Suzuki couplings", ChemComm, 2003, 2652-2653.

Antonia F. Stepan, "Pd-Containing Perovksites: New Catalyst for Suzuki Coupling Reactions", Pembroke College, Mar. 2004.

* cited by examiner

*Primary Examiner*—Daniel M Sullivan
*Assistant Examiner*—Yate' K Cutliff
(74) *Attorney, Agent, or Firm*—Jean C. Edwards, Esq.; Akerman Senterfitt

(57) ABSTRACT

To provide a catalyst for synthesis reaction which can achieve good yield in the Sonogashira reaction and also can be recovered after the reaction, and a method for synthesizing a compound in which the catalyst for synthesis reaction is used, a perovskite-type composite oxide containing palladium is used as the catalyst for synthesis reaction in the Sonogashira reaction represented by the following reaction scheme (1):

$$R_1-X + HC\equiv CR_2 \rightarrow R_1C\equiv CR_2 \qquad (1)$$

4 Claims, 5 Drawing Sheets

METHOD FOR SYNTHESIZING COMPOUND AND CATALYST FOR SYNTHESIS REACTION

CROSS-REFERENCE TO RELATED APPLICATIONS

The present application is a 35 U.S.C. 371 national stage entry of International Patent Application No. PCT/JP2005/008317, filed Apr. 25, 2005, which claims priority from Japanese Patent Application No. JP 2004-132553, filed Apr. 28, 2004, the contents of which are herein incorporated by reference in their entirety.

The present invention relates to a method for synthesizing a compound, and a catalyst for synthesis reaction and, more particularly, to a method for synthesizing a compound by the Sonogashira reaction, and a catalyst for synthesis reaction used in the method for the synthesizing same.

BACKGROUND OF THE INVENTION

Heretofore, the Sonogashira reaction has widely been known as a coupling reaction of an alkyne and has been used in a synthesis of a biologically active substance having an acetylene skeleton in the molecule, or an organic functional material.

In this Sonogashira reaction, palladium as a catalyst and copper as a promoter are usually used in combination. In practice, for example, tetrakis(triphenylphosphine)palladium, dichlorobis(triphenylphosphine)palladium and copper iodide are used in combination (see, for example, Japanese Unexamined Patent Publication No. Hei 10-114691).

However, since palladium is expensive, it is desired that palladium is recovered after the reaction and used again so as to reduce the production cost.

However, in the actual reaction, palladium is used in the form of an organic metal complex, which is soluble in an organic solvent, such as tetrakis(triphenylphosphine)palladium or dichlorobis(triphenylphosphine)palladium, as described above. Therefore, it is difficult to recover palladium and the organic metal complex is discarded as it is after the reaction.

An object of the present invention is to provide a catalyst for synthesis reaction which can achieve good yield in the Sonogashira reaction and also can be recovered after the reaction, and a method for synthesizing a compound in which the catalyst for synthesis reaction is used.

SUMMARY OF THE INVENTION

A method for synthesizing a compound of the present invention comprises the step of reacting a compound represented by the following general formula (1) with a compound represented by the following general formula (2) in the presence of a perovskite-type composite oxide containing palladium:

$$R_1\text{—}X \quad (1)$$

wherein $R_1$ represents an aryl group which may have a substituent, a heterocyclic group which may have a substituent or an alkenyl group which may have a substituent, and X represents a halogen atom excluding fluorine, a trifluoromethanesulfonyloxy group, a p-toluenesulfonyloxy group or a methanesulfonyloxy group, and $$HC\text{≡}CR_2 \quad (2)$$

wherein $R_2$ represents a hydrogen atom, an aryl group which may have a substituent, a heterocyclic group which may have a substituent, an alkyl group which may have a substituent, an alkenyl group which may have a substituent, an alkynyl group which may have a substituent or trialkyl-substituted silyl group.

In the method for synthesizing a compound of the present invention, the perovskite-type composite oxide containing palladium is preferably represented by the following general formula (3), more preferably represented by the following general formula (4), and particularly preferably represented by the following general formula (5):

$$AB_{1-z}Pd_zO_3 \quad (3)$$

wherein A represents at least one element selected from rare-earth elements and alkaline earth metals, B represents at least one element selected from transition elements (excluding rare-earth elements and Pd) and Al, and z represents an atomic ratio of Pd, $$A_{1-x}A'_xB_{1-(y+z)}Cu_yPd_zO_3 \quad (4)$$

wherein A represents at least one element selected from rare-earth elements, A' represents at least one element selected from alkaline earth metals, B represents at least one element selected from transition elements (excluding rare-earth elements, Cu and Pd) and Al, x represents an atomic ratio satisfying the following relation: $0 \leq x \leq 0.5$, y represents an atomic ratio satisfying the following relation: $0 < y \leq 0.5$, and z represents an atomic ratio satisfying the following relation: $0 < z \leq 0.5$, and $$AB_{1-(y+z)}Cu_yPd_zO_3 \quad (5)$$

wherein A represents at least one element selected from Y, La, Ce, Pr and Nd, B represents at least one element selected from Mn, Fe, Co and Al, y represents an atomic ratio satisfying the following relation: $0 < y \leq 0.5$ and z represents an atomic ratio satisfying the following relation: $0 < z \leq 0.5$.

The present invention also includes a catalyst for synthesis reaction, comprising a perovskite-type composite oxide containing palladium, used for reacting a compound represented by the following general formula (1) with a compound represented by the following general formula (2):

$$R_1\text{—}X \quad (1)$$

wherein $R_1$ represents an aryl group which may have a substituent, a heterocyclic group which may have a substituent or an alkenyl group which may have a substituent, and X represents a halogen atom excluding fluorine, a trifluoromethanesulfonyloxy group, a p-toluenesulfonyloxy group or a methanesulfonyloxy group, and $$HC\text{≡}CR_2 \quad (2)$$

wherein $R_2$ represents a hydrogen atom, an aryl group which may have a substituent, a heterocyclic group which may have a substituent, an alkyl group which may have a substituent, an alkenyl group which may have a substituent, an alkynyl group which may have a substituent or a trialkyl-substituted silyl group.

The catalyst for synthesis reaction of the present invention is preferably represented by the following general formula (3), more preferably represented by the following general formula (4), and particularly preferably represented by the following general formula (5):

$$AB_{1-z}Pd_zO_3 \qquad (3)$$

wherein A represents at least one element selected from rare-earth elements and alkaline earth metals, B represents at least one element selected from transition elements (excluding rare-earth elements and Pd) and Al, and z represents an atomic ratio of Pd, $$A_{1-x}A'_xB_{1-(y+z)}Cu_yPd_zO_3 \qquad (4)$$

wherein A represents at least one element selected from rare-earth elements, A' represents at least one element selected from alkaline earth metals, B represents at least one element selected from transition elements (excluding rare-earth elements, Cu and Pd) and Al, x represents an atomic ratio satisfying the following relation: $0 \leqq x \leqq 0.5$, y represents an atomic ratio satisfying the following relation: $0 < y \leqq 0.5$, and z represents an atomic ratio satisfying the following relation: $0 < z \leqq 0.5$, and $$AB_{1-(y+z)}Cu_yPd_zO_3 \qquad (5)$$

wherein A represents at least one element selected from Y, La, Ce, Pr and Nd, B represents at least one element selected from Mn, Fe, Co and Al, y represents an atomic ratio satisfying the following relation: $0 < y \leqq 0.5$, and z represents an atomic ratio satisfying the following relation: $0 < z \leqq 0.5$.

In the method for synthesizing a compound of the present invention, the compound can be synthesized by the Sonogashira reaction in a good yield in the presence of a perovskite-type composite oxide containing palladium. Further, the peroyskite-type composite oxide containing palladium can be recovered after the reaction. Therefore, it becomes possible to reduce the environmental burden due to discharge of the catalyst for the synthesis reaction and to reduce the cost due to reuse.

DESCRIPTION OF THE INVENTION

Figure 1:
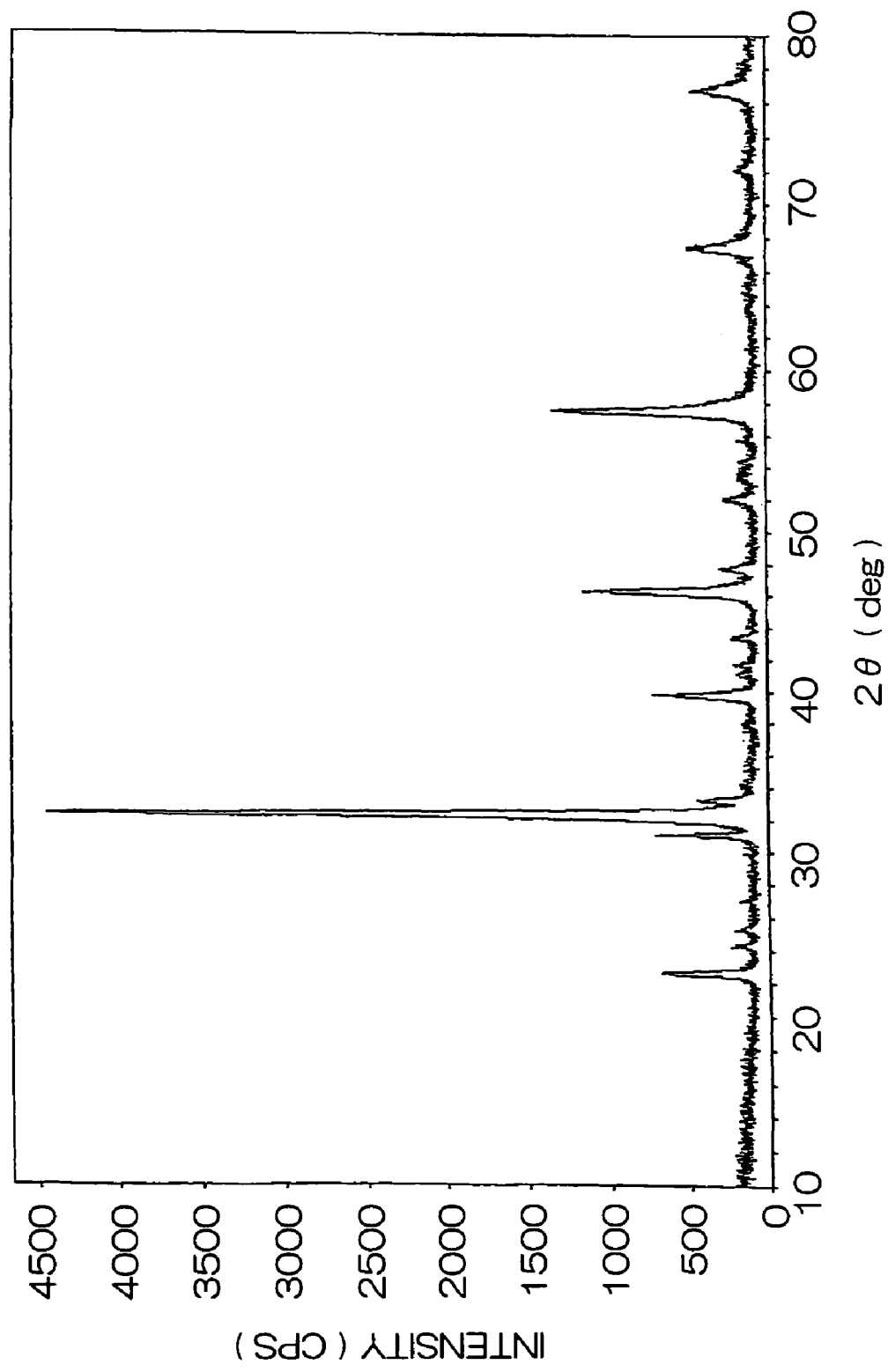
FIG. 1 is a graph showing an X-ray diffraction spectrum of a powder of Production Example 1.

The catalyst for synthesis reaction of the present invention comprises a perovskite-type composite oxide containing palladium (Pd).

In the present invention, the perovskite-type composite oxide containing palladium is a composite oxide having a perovskite-type structure represented by a general formula $ABO_3$ and can be used without being limited as long as the perovskite-type composite oxide contains palladium.

Examples of the perovskite-type composite oxide containing palladium include, for example, a perovskite-type composite oxide containing palladium as a constituent so that palladium constitutes a constituent element of the perovskite-type composite oxide, and a perovskite-type composite oxide supporting palladium wherein palladium is later supported by the perovskite-type composite oxide.

The perovskite-type composite oxide containing palladium as a constituent is represented, for example, by the following general formula (3):

$$AB_{1-z}Pd_zO_3 \qquad (3)$$

wherein A represents at least one element selected from rare-earth elements and alkaline earth metals, B represents at least one element selected from transition elements (excluding rare-earth elements and Pd) and Al, and z represents an atomic ratio of Pd.

In the general formula (3), examples of the rare-earth elements represented by A include Sc (scandium), Y (yttrium), La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium) and Lu (lutetium), of which Y, La, Ce, Pr and Nd are preferable.

These rare-earth elements can be used alone or in combination.

In the general formula (3), examples of the alkaline earth metals represented by A include Be (beryllium), Mg (magnesium), Ca (calcium), Sr (strontium), Ba (barium) and Ra (radium), of which Sr is preferable.

These alkaline earth metals can be used alone or in combination.

In the general formula (3), the alkaline earth metals represented by A are preferably used in an atomic ratio of 0.5 or less based on the rare-earth elements and, more preferably, the rare-earth elements are used alone.

Examples of the transition elements (excluding rare-earth elements and Pd) represented by B in the general formula (3) include elements (excluding Pd) having atomic numbers of 22 (Ti) through 30 (Zn), atomic numbers of 40 (Zr) through 48 (Cd) and atomic numbers of 72 (Hf) through 80 (Hg) in the Periodic Table of Elements (IUPAC, 1990).

Preferred examples of the transition elements (excluding rare-earth elements and Pd) and Al represented by B include Cu (copper) as an essential element and the transition elements selected from Cr (chromium), Mn (manganese), Fe (iron), Co (cobalt), Ni (nickel), Zn (zinc) and Al (aluminum) as an optional element, and more preferred examples include Cu as an essential element and the transition elements selected from Mn, Fe, Co and Al as an optional element.

The perovskite-type composite oxide containing palladium as a constituent can be prepared according to any suitable procedure for production of composite oxides. Examples thereof include a coprecipitation process, a citrate complex process and an alkoxide process, without being limited to any particular process.

In the coprecipitation process, for example, an aqueous mixed salt solution containing salts of the above-mentioned respective elements in a predetermined stoichiometric ratio is initially prepared. The aqueous mixed salt solution is coprecipitated by addition of a neutralizing agent, and the resulting coprecipitate is dried and heat-treated.

Examples of the salts of the respective elements include inorganic salts such as sulfates, nitrates, chlorides and phosphates; and organic acid salts such as acetates and oxalates. The aqueous mixed salt solution can be prepared, for example, by adding the salts of the respective elements to water in such proportions as to establish a predetermined stoichiometric ratio and mixing them with stirring.

Subsequently, the aqueous mixed salt solution is coprecipitated by adding the neutralizing agent thereto. The neutralizing agent includes ammonia; organic bases including amines such as triethylamine and pyridine; and inorganic bases such as sodium hydroxide, potassium hydroxide, potassium carbonate and ammonium carbonate. The neutralizing agent is added so that the solution after the addition of the neutralizing agent has a pH of about 6 to about 10.

The resulting coprecipitate is, where necessary, washed with water, is dried, for example, by vacuum drying or forced-air drying and is then heat-treated at about 500 to 1000° C., and preferably at about 600 to about 950° C. The perovskite-type composite oxide can thus be prepared.

In the citrate complex process, for example, an aqueous citrate mixed salt solution in a predetermined stoichiometric ratio of the respective elements is prepared by adding a citric acid and the salts of the above-mentioned respective elements. Then, the aqueous citrate mixed salt solution is evaporated to dryness to form a citrate complex of the above-mentioned respective elements, and the resulting citrate complex is provisionally baked and is heat-treated.

The same as listed above can be used as the salts of the respective elements herein. The aqueous citrate mixed salt solution can be prepared, for example, by initially preparing an aqueous mixed salt solution by the above procedure and adding an aqueous solution of citric acid to the aqueous mixed salt solution.

Then, the aqueous citrate mixed salt solution is evaporated to dryness to form a citrate complex of the above-mentioned respective elements. The evaporation to dryness is carried out at a temperature at which the formed citrate complex is not decomposed, such as at room temperature to about 150° C., thereby to remove the fluid immediately. The citrate complex of the above-mentioned respective elements is thus obtained.

The formed citrate complex is then provisionally baked and is then heat-treated. The provisional baking may be carried out, for example, by heating at 250° C. or higher in vacuum or in an inert atmosphere. The provisionally baked article is then heat-treated, for example, at about 500 to 1000° C., and preferably at about 600 to 950° C. to obtain the perovskite-type composite oxide.

In the alkoxide process, for example, a mixed alkoxide solution containing alkoxides of the above-mentioned respective elements excluding the noble metals including Pd in the above-mentioned stoichiometric ratio is prepared, and the mixed alkoxide solution is precipitated on hydrolysis by adding an aqueous solution containing salts of the noble metals including Pd thereto, and the resulting precipitate is dried and then heat-treated.

Examples of the alkoxides of the respective elements include alcoholates each comprising the respective element and an alkoxy such as methoxy, ethoxy, propoxy, isopropoxy or butoxy; and alkoxyalcoholates of the respective elements represented by the following general formula (6):

$$E[OCH(R_3)-(CH_2)_i-OR_4]_j \quad (6)$$

wherein E represents the respective element, $R_3$ represents a hydrogen atom or an alkyl group having 1 to 4 carbon atoms, $R_4$ represents an alkyl group having 1 to 4 carbon atoms, i represents an integer of 1 to 3, and j represents an integer of 2 to 3.

More specific examples of the alkoxyalcoholates include methoxyethylate, methoxypropylate, methoxybutylate, ethoxyethylate, ethoxypropylate, propoxyethylate and butoxyethylate.

The mixed alkoxide solution can be prepared, for example, by adding the alkoxides of the respective elements to an organic solvent so as to establish the above-mentioned stoichiometric ratio and mixing them with stirring.

The organic solvent is not specifically limited, as long as it can dissolve the alkoxides of the respective elements. Examples of such organic solvents include aromatic hydrocarbons, aliphatic hydrocarbons, alcohols, ketones and esters. Among these organic solvents, aromatic hydrocarbons such as benzene, toluene and xylenes are preferred.

Subsequently, the mixed alkoxide solution is precipitated by adding an aqueous solution containing salts of the noble metals including Pd in a predetermined stoichiometric ratio. Examples of the aqueous solution containing salts of the noble metals including Pd include aqueous nitrate solution, aqueous chloride solution, aqueous hexaammine chloride solution, aqueous dinitrodiammine nitrate solution, hexachloro acid hydrate and potassium cyanide salt.

The resulting precipitate is then dried, for example, by vacuum drying or forced-air drying and is heat-treated, for example, at about 500 to 1000° C., and preferably at about 500 to 850° C. Thus, the perovskite-type composite oxide can be prepared.

In the alkoxide process, the perovskite-type composite oxide may be alternatively prepared in the following manner, for example. A solution containing organometal salts of the noble metals including Pd is added to the above-mentioned mixed alkoxide solution to obtain a homogenous mixed solution. The homogenous mixed solution is precipitated by adding water thereto. The resulting precipitate is dried and then heat-treated.

Examples of the organometal salts of the noble metals including Pd include carboxylic acid salts of the noble metals including Pd derived from, for example, acetate or propionate; and metal chelate complexes of the noble metals including Pd such as diketone complexes of the noble metals including Pd derived from, diketone compounds represented by the following general formula (7) or (8):

$$R_5COCHR_7COR_6 \quad (7)$$

wherein $R_5$ represents an alkyl group having 1 to 4 carbon atoms, a fluoroalkyl group having 1 to 4 carbon atoms or an aryl group, $R_6$ represents an alkyl group having 1 to 4 carbon atoms, a fluoroalkyl group having 1 to 4 carbon atoms, aryl group or an alkyloxy group having 1 to 4 carbon atoms, and $R_7$ represents a hydrogen atom or an alkyl group having 1 to 4 carbon atoms, and

$$CH_3CH(COR_8)_2 \quad (8)$$

wherein R8 represents a hydrogen atom or an alkyl group having 1 to 4 carbon atoms.

In the above-mentioned general formulas (7) and (8), examples of the alkyl groups each having 1 to 4 carbon atoms as $R_5$, $R_6$, $R_7$ and $R_8$ include methyl, ethyl, propyl, isopropyl, n-butyl, s-butyl and t-butyl. The fluoroalkyl groups each having 1 to 4 carbon atoms as $R_5$ and $R_6$ include, for example, trifluoromethyl. The aryl groups as $R_5$ and R6 include, for example, phenyl. The alkyloxy group having 1 to 4 carbon atoms as $R_6$ includes, for example, methoxy, ethoxy, propoxy, isopropoxy, n-butoxy, s-butoxy and t-butoxy.

More specific examples of the diketone compounds include 2,4-pentanedione, 2,4-hexanedione, 2,2-dimethyl-3,5-hexanedione, 1-phenyl-1,3-butanedione, 1-trifluoromethyl-1,3-butanedione, hexafluoroacetylacetone, 1,3-diphenyl-1,3-propanedione, dipivaloylmethane, methyl acetoacetate, ethyl acetoacetate and t-butyl acetoacetate.

The solution containing the organometal salts of the noble metals including Pd can be prepared, for example, by adding the organometal salts of the noble metals including Pd to an organic solvent so as to establish the above-mentioned stoichiometric ratio and mixing them with stirring. The same as listed above can be used as the organic solvent herein.

Thus-prepared solution containing the organometal salts of the noble metals including Pd is mixed with the above-mentioned mixed alkoxide solution to prepare a homogenous mixed solution, and the homogenous mixed solution is precipitated by adding water thereto. The resulting precipitate is dried, for example, by vacuum drying or forced-air drying and is then heat-treated at about 400 to 1000° C., and preferably at about 500 to 850° C. Thus, the perovskite-type composite oxide can be prepared.

Examples of the perovskite-type composite oxide supporting palladium include perovskite-type composite oxides represented by the following general formula (9) each of which supports Pd:

$$ABO_3 \tag{9}$$

wherein A represents at least one element selected from rare-earth elements and alkaline earth metals, and B represents at least one element selected from transition elements (excluding rare-earth elements and Pd) and Al.

The same as listed above can be used as the rare-earth elements and the alkaline earth metals represented by A, and the transition elements represented by B (excluding rare-earth elements and Pd) and Al, in the general formula (9). B preferably includes at least Cu.

These perovskite-type composite oxides can be prepared by a suitable process for production of composite oxides such as a coprecipitation process, a citrate complex process or an alkoxide process, as in the above processes. In the alkoxide process, a mixed alkoxide solution may be hydrolyzed by adding water thereto.

Palladium can be supported by the resulting perovskite-type composite oxide according to any known process, without being limited to a particular process. Palladium can be supported, for example, by preparing a salt solution containing palladium, impregnating the perovskite-type composite oxide with this salt-containing solution and then baking the impregnated composite oxide. An amount of palladium to the perovskite-type composite oxide is, for example, 20 parts by weight or less, and preferably 0.5 to 5 parts by weight, based on 100 parts by weight of the perovskite-type composite oxide.

Of the above-mentioned perovskite-type composite oxides, the perovskite-type composite oxides each comprising palladium as a constituent are preferably used.

In the perovskite-type composite oxides containing palladium as a constituent, a perovskite-type composite oxide represented by the following general formula (4) is preferably used and a perovskite-type composite oxide represented by the following general formula (5) is particularly preferably used:

$$A_{1-x}A'_xB_{1-(y+z)}Cu_yPd_zO_3 \tag{4}$$

wherein A represents at least one element selected from rare-earth elements, A' represents at least one element selected from alkaline earth metal, B represents at least one element selected from transition elements (excluding rare-earth elements, Cu and Pd) and Al, x represents an atomic ratio satisfying the following relation: $0 \leq x \leq 0.5$, y represents an atomic ratio satisfying the following relation: $0 < y \leq 0.5$, and z represents an atomic ratio satisfying the following relation: $0 < z \leq 0.5$, and $$AB_{1-(y+z)}Cu_yPd_zO_3 \tag{5}$$

wherein A represents at least one element selected from Y, La, Ce, Pr and Nd, B represents at least one element selected from Mn, Fe, Co and Al, y represents an atomic ratio satisfying the following relation: $0 < y \leq 0.5$ and z represents an atomic ratio satisfying the following relation: $0 < z \leq 0.5$.

More specific examples of the perovskite-type composite oxide containing palladium as a constituent include $La_{1.00}Fe_{0.57}Cu_{0.38}Pd_{0.05}O_3$, $La_{0.90}Ce_{0.10}Fe_{0.57}Cu_{0.38}Pd_{0.05}O_3$, $La_{1.00}Fe_{0.57}Co_{0.38}Pd_{0.05}O_3$, $La_{1.00}Fe_{0.95}Pd_{0.05}O_3$, $La_{1.00}Cu_{0.95}Pd_{0.05}O_3$, $La_{0.090}Ce_{0.10}Al_{0.95}Pd_{0.05}O_3$, $La_{1.00}Fe_{0.57}Mn_{0.38}Pd_{0.05}O_3$, $La_{1.00}Mn_{0.95}Pd_{0.05}O_3$, $La_{1.00}Co_{0.95}Pd_{0.05}O_3$, $Pr_{0.90}Sr_{0.10}Mn_{0.90}Pd_{0.10}O_3$ and $Nd_{0.50}Y_{0.50}Fe_{0.57}CU_{0.38}Pd_{0.05}O_3$.

The catalyst for synthesis reaction of the present invention is used for reacting a compound represented by the following general formula (1) with a compound represented by the following general formula (2):

$$R_1-X \tag{1}$$

wherein $R_1$ represents an aryl group which may have a substituent, a heterocyclic group which may have a substituent or an alkenyl group which may have a substituent, and X represents a halogen atom excluding fluorine, a trifluoromethanesulfonyloxy group, a p-toluenesulfonyloxy group or a methanesulfonyloxy group, and $$HC \equiv CR_2 \tag{2}$$

wherein $R_2$ represents a hydrogen atom, an aryl group which may have a substituent, a heterocyclic group which may have a substituent, an alkyl group which may have a substituent, an alkenyl group which may have a substituent, an alkynyl group which may have a substituent or a trialkyl-substituted silyl group.

Examples of the aryl group of the aryl group which may have a substituent represented by $R_1$ of the general formula (1) and $R_2$ of the general formula (2) include aryl groups each having 6 to 14 carbon atoms, such as phenyl, tolyl, xylyl, biphenyl, naphthyl, anthryl, phenanthryl and azulenyl.

The substituent of the aryl group is not specifically limited and appropriately includes substituents corresponding to the purpose and use thereof, such as hydrocarbon group and hetero atom-containing hydrocarbon group. Examples of the substituent include alkyl groups each having 1 to 4 carbon atoms such as methyl, ethyl, n-propyl, isopropyl, butyl, isobutyl, sec-butyl and tert-butyl; allylenyl groups each having 2 to 4 carbon atoms such as vinyl, 1-methylvinyl, 1-propenyl and allyl; alkynyl groups each having 2 to 4 carbon atoms such as ethynyl, 1-propynyl and 1-propargyl; cycloalkyl groups each having 3 to 6 carbon atoms such as cyclopropyl, cyclobutyl, cyclopentyl and cyclohexyl; cycloalkenyl groups each having 5 to 7 carbon atoms such as cyclopentenyl and cyclohexenyl; aralkyl groups each having 7 to 11 carbon atoms such as benzyl, α-methylbenzyl and phenethyl group; phenyl groups; alkoxy groups each having 1 to 6 carbon atoms such as methoxy, ethoxy, propoxy, iso-propoxy, n-butoxy, iso-butoxy, sec-butoxy and tert-butoxy; phenoxy groups; alkanoyl groups having 1 to 6 carbon atoms such as formyl, acetyl, propionyl, n-butyryl and iso-butyryl group; benzoyl group; alkanoyloxy groups having 1 to 6 carbon atoms such as formyloxy, acetyloxy, propionyloxy, n-butyryloxy and isobutyryloxy group; benzoyloxy groups; carboxyl groups; alkoxycarbonyl group having 2 to 7 carbon atoms such as methoxycarbonyl, ethoxycarbonyl, n-propoxycarbonyl, isopropoxycarbonyl, n-butoxycarbonyl, isobutoxycarbonyl and tert-butoxycarbonyl; carbamoyl groups; N-mono-$C_{1-4}$ alkylcarbamoyl groups such as N-methylcarbamoyl, N-ethylcarbamoyl, N-propylcarbamoyl, N-isopropylcarbamoyl and N-butylcarbamoyl; N,N-di-$C_{1-4}$ alkylcarbamoyl groups such as N,N-dimethylcarbamoyl, N,N-diethylcarbamoyl, N,N-dipropylcarbamoyl and N,N-dibutylcarbamoyl; cyclic aminocarbonyl such as 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl; halogen atoms such as fluorine, chlorine, bromine and iodine; mono-, di-, or tri-halogeno-$C_{1-4}$ alkyl groups such as chloromethyl, dichloromethyl, trifluoromethyl and trifluoroethyl; oxo groups; amidino groups; imino groups; amino groups; mono-$C_{1-4}$ alkylamino groups such as methylamino, ethylamino, propylamino, isopropylamino and butylamino; di-$C_{1-4}$ alkylamino groups such as dimethylamino, diethylamino, dipropylamino, diisopropylamino and dibutylamino; 3 to 6-membered cyclic amino groups, which may have, other than carbon atoms and one nitrogen atom, 1 to 3 hetero atoms selected from oxygen atom, sulfur atom and nitrogen atom, such as aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl; alkanoylamide groups having 1 to 6 carbon atoms such as formamide, acetamido, trifluoroacetamido, propionylamide, butyrylamide and isobutyrylamide; benzamide groups; carbamoylamino groups; N-$C_{1-4}$ alkylcarbamoylamino groups such as N-methylcarbamoylamino, N-ethylcarbamoylamino, N-propylcarbamoylamino, N-isopropylcarbamoylamino and N-butylcarbamoylamino; N,N-di-$C_{1-4}$ alkylcarbamoylamino groups such as N,N-dimethylcarbamoylamino, N,N-diethylcarbamoylamino, N,N-dipropylcarbamoylamino and N,N-dibutylcarbamoylamino; alkylenedioxy groups each having 1 to 3 carbon atoms such as methylenedioxy and ethylenedioxy group; hydroxy groups; epoxy groups (—O—); nitro groups; cyano groups; mercapto groups; sulfo groups; sulfino groups; phosphono groups; sulfamoyl groups; monoalkylsulfamoyl groups each having 1 to 6 carbon atoms such as N-methylsulfamoyl, N-ethylsulfamoyl, N-propylsulfamoyl, N-isopropylsulfamoyl and N-butylsulfamoyl; di-$C_{1-4}$ alkylsulfamoyl groups such as N,N-dimethylsulfamoyl, N,N-diethylsulfamoyl, N,N-dipropylsulfamoyl and N,N-dibutylsulfamoyl; alkylthio groups each having 1 to 6 carbon atoms such as methylthio, ethylthio, propylthio, isopropylthio, n-butylthio, sec-butylthio and tert-butylthio; phenylthio groups; alkylsulfinyl groups each having 1 to 6 carbon atoms such as methylsulfinyl, ethylsulfinyl, propylsulfinyl and butylsulfinyl group; phenylsulfinyl groups; alkylsulfonyl groups each having 1 to 6 carbon atoms such as methylsulfonyl, ethylsulfonyl, propylsulfonyl and butylsulfonyl; and phenylsulfonyl groups. These substituents may have 1 to 5 substituents.

Examples of the heterocyclic group of the heterocyclic group which may have a substituent represented by $R_1$ of the general formula (1) and $R_2$ of the general formula (2) include 5-membered ring groups having, other than carbon atoms, 1 to 4 hetero atoms selected from oxygen atom, sulfur atom and nitrogen atom, such as 2- or 3-thienyl, 2- or 3-furyl, 2- or 3-pyronyl, 2-, 3- or 4-pyridyl, 2-, 4- or 5-oxazolyl, 2-, 4- or 5-thiazolyl, 3-, 4-, or 5-pyrazolyl, 2-, 4- or 5-imidazolyl, 3-, 4- or 5-isooxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl; 6-membered ring groups having, other than carbon atoms, 1 to 4 hetero atoms selected from oxygen atom, sulfur atom and nitrogen atom, such as N-oxide-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl and N-oxide-3- or 4-pyridazinyl; and 5- to 8-membered ring groups having carbon atoms, carbon atoms of dicyclic or tricyclic condensed ring groups having 1 to 4 hetero atoms selected from oxygen atom, sulfur atom and nitrogen atom and 1 to 4 hetero atoms such as oxygen atom, sulfur atom and nitrogen atom, such as benzofuryl, benzothiazolyl, benzooxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolidinyl, 1,8-naphthylidinyl, purinyl, pteridinyl, dibenzofuranyl, carbazolyl, acridinyl, phenanthridinyl, chromanyl, benzooxazinyl, phenazinyl, phenothiazinyl and phenoxazinyl, or condensed rings thereof.

The substituent of the heterocyclic group is not specifically limited and appropriately includes substituents corresponding to the purpose and use thereof, such as hydrocarbon group and hetero atom-containing hydrocarbon group. Examples of the substituent include the same as listed above. The heterocyclic group may have 1 to 5 substituents.

Examples of the alkenyl group of the alkenyl group which may have a substituent represented by $R_1$ of the general formula (1) and $R_2$ of the general formula (2) include alkenyl groups each having 2 to 18 carbon atoms such as vinyl, allyl, metallyl, isopropenyl, 1-propenyl, 2-propenyl, 2-methyl-1-propenyl, butenyl, pentenyl, hexenyl, heptynyl, octenyl, nonenyl, decenyl, undecenyl, dodecenyl, tetradecenyl, hexadecenyl and octadecenyl.

The substituent of the alkenyl group is not specifically limited and appropriately includes substituents corresponding to the purpose and use thereof, such as hydrocarbon group and hetero atom-containing hydrocarbon group. Examples of the substituent include the same as listed above. The heterocyclic group may have 1 to 5 substituents.

Examples of the alkyl group of the alkyl group which may have a substituent represented by $R_2$ of the general formula (2) include alkyl groups each having 1 to 18 carbon atoms such as methyl, ethyl, propyl, iso-propyl, n-butyl, iso-butyl, sec-butyl, tert-butyl, pentyl, iso-pentyl, sec-pentyl, hexyl, heptyl, n-octyl, isooctyl, 2-ethylhexyl, nonyl, decyl, isodecyl, dodecyl, tetradecyl, hexadecyl and octadecyl.

The substituent of the alkyl group is not specifically limited and appropriately includes substituents corresponding to the purpose and use thereof, such as hydroxyl group, hydrocarbon group and hetero atom-containing hydrocarbon group. Examples of the substituent include the same as listed above. The heterocyclic group may have 1 to 5 substituents. Examples of the alkyl group which may have a hydroxyl group include 1-hydroxy and 1-methylethyl.

Examples of the alkynyl group of the alkynyl group which may have a substituent represented by $R_2$ of the general formula (2) include alkynyl groups each having 2 to 10 carbon atoms such as ethynyl, 2-propynyl, 3-hexynyl and 1-octenyl.

The substituent of the alkynyl group is not specifically limited and appropriately includes substituents corresponding to the purpose and use thereof, such as hydrocarbon group and hetero atom-containing hydrocarbon group. Examples of the substituent include the same as listed above. The heterocyclic group may have 1 to 5 substituents.

Examples of the trialkyl-substituted silyl group represented by $R_2$ of the general formula (2) include silyl groups each being substituted with 3 alkyl groups having 1 to 10 carbon atoms, such as trimethylsilyl group, triethylsilyl group, tripropylsilyl group, dimethyl t-butylsilyl group and tridecylsilyl group.

Examples of the halogen atom excluding fluorine represented by X of the general formula (1) include chlorine, bromine and iodine.

A compound represented by the general formula (1) is reacted with a compound represented by the general formula (2) to produce a compound represented by the following general formula (10):

  (10)

wherein $R_1$ and $R_2$ are as defined above.

In the method for synthesizing a compound of the present invention, the reaction of a compound represented by the general formula (1) and a compound represented by the general formula (3) is conducted according to the Sonogashira reaction shown in the following reaction scheme (1), and is conducted in the presence of the perovskite-type composite oxide containing palladium as the catalyst for synthesis reaction of the present invention, and a base.

  (1)

In this reaction, examples of the base include ammonia; di- or trialkylamines such as diethylamine and triethylamine; organic bases such as pyridine, morpholine, quinoline, piperidine, DBU (diazabicycloundecene) and anilines; and inorganic bases, for example, hydroxides such as sodium hydroxide and potassium hydroxide; carbonates such as sodium carbonate ($Na_2CO_3$), potassium carbonate ($K_2CO_3$) and cesium carbonate ($Cs_2CO_3$); and phosphates such as sodium phosphate ($Na_3PO_4$) and potassium phosphate ($K_3PO_4$). These bases can be used alone or in combination.

In this reaction, a proportion of the compound represented by the general formula (1) to the compound represented by the general formula (2) is not specifically limited and a proportion of the compound represented by the general formula (2) is from 0.1 to 10 equivalents, and preferably from 0.5 to 3 equivalents, based on the compound represented by the general formula (1).

In this reaction, a proportion of the perovskite-type composite oxide containing palladium is not specifically limited and is added in the proportion in a range from 0.001 to 10 mol %, and preferably from 0.1 to 5 mol %, in terms of the palladium content.

In this reaction, a proportion of the base is not specifically limited and the base may be, if necessary, used in a large amount of 1 equivalent or more, for example, as a reaction solvent.

This reaction is conducted, for example, under the conditions of a reaction pressure of 0 to 5000 KPa, preferably 0 to 3000 KPa, a reaction temperature of −20 to 250° C., preferably 0 to 180° C., and a reaction time of 0.1 to 72 hours, preferably 0.5 to 24 hours.

It is effective to heat by irradiation with microwave so as to accelerate the reaction.

In this reaction, a reaction solvent may be used. Examples of the reaction solvent include water, protic polar solvents including alcohols such as methanol, ethanol, isopropanol (IPA) and glycol; aprotic polar solvents such as N,N-dimethylformamide (DMF), N,N-dimethylacetamide (DMAC), dimethyl sulfoxide (DMSO), N-methyl pyrrolidone (NMP), acetonitrile and piperidine; above-mentioned amines; ethers such as dioxane and tetrahydrofuran (THF); and aromatic hydrocarbons such as benzene, toluene and xylene. These reaction solvents may be used alone or in combination.

In this reaction, an additive can be added so as to accelerate the reaction. Examples of the additive include organic ammonium halides such as tetra-n-butylammonium bromide (TBAB). The additive is added in the proportion of 1 to 200 mol %.

More specifically, in this reaction, for example, a compound represented by the general formula (1) and a compound represented by the general formula (2) are added to a reaction solvent in the proportions described above, together with a perovskite-type composite oxide containing palladium and a base, and the mixture is reacted under the conditions described above, a compound represented by the general formula (10) can be obtained.

In the method for synthesizing a compound of the present invention a compound represented by the general formula (10) can be synthesized by the Sonogashira reaction in a good yield in the presence of a perovskite-type composite oxide containing palladium.

In the method for synthesizing a compound of the present invention, the perovskite-type composite oxide containing palladium is solid after the completion of the reaction and can be easily recovered from the reaction mixture by filtration or decantation. Therefore, it becomes possible to reduce environmental burden due to discharge of the catalyst for synthesis reaction and to reduce the cost due to reuse.

Therefore, the method for synthesizing a compound of the present invention is fit for various uses where the Sonogashira reaction is industrially used such as synthesis of drug intermediates, synthetic polymer materials, liquid crystal materials and optical materials.

EXAMPLES

The present invention will be illustrated in further detail by way of the following Examples, which by no means limit the scope of the present invention.

1) Production Example of Catalyst for Synthesis Reaction (Perovskite-Type Composite Oxide)

Production Example 1 (Production of $La_{1.00}Fe_{0.57}Cu_{0.38}Pd_{0.05}O_3$)

| Lanthanum nitrate hexahydrate | 1.73 g (0.0040 mol) |
| Iron nitrate nonahydrate | 0.92 g (0.0023 mol) |
| Copper nitrate trihydrate | 0.37 g (0.0015 mol) |
| Palladium nitrate | 0.046 g (0.0002 mol) |

A mixed salt solution was prepared by charging the above components in a 500 mL beaker, and dissolving them in 50 mL of dilute nitric acid. Then, 50 mL of an aqueous 0.5 mol/L citric acid solution prepared in another beaker was added to 50 mL of the mixed salt solution to prepare an aqueous citrate salt solution.

Entire water was evaporated to dryness by continuously stirring this 500 mL beaker on a heating plate at 120° C. The residue was recovered and the entire organic substance was evaporated to dryness by subjecting to heat treatment at 400° C. for 4 hours using an electric furnace.

The resulting precursor of the LaFeCuPd composite oxide was powdered, pelletized and then subjected to heat treatment in the atmosphere at 700° C. for 4 hours using an electric furnace to obtain a blackish brown powder.

An X-ray powder diffraction analysis of the powder was conducted. As a result, it was identified as a single crystal phase comprising a composite oxide having a perovskite-type structure of $La_{1.00}Fe_{0.57}Cu_{0.38}Pd_{0.05}O_3$. The powder was found to have a specific surface area of 18 m$^2$/g and a Pd content in the composite oxide of 2.14% by mass. FIG. 1 is a graph showing this X-ray diffraction spectrum.

Production Example 2 (Production of $La_{1.00}Fe_{0.57}Co_{0.38}Pd_{0.05}O_3$)

| | |
|---|---|
| Lanthanum ethoxyethylate | 40.7 g (0.100 mol) |
| Iron ethoxyethylate | 18.4 g (0.057 mol) |
| Cobalt ethoxyethylate | 9.0 g (0.038 mol) |

A mixed alkoxide solution was prepared by charging the above components in a 500 mL round-bottomed flask and dissolving them in 200 mL of toluene with stirring.

Separately, 1.52 g (0.005 mol) of palladium acetylacetonate was dissolved in 100 mL of toluene and the resulting solution was added to the mixed alkoxide solution to obtain a homogenous mixed solution containing LaFeCoPd. Next, 200 mL of deionized water was added dropwise to the homogeneous mixed solution over about 15 minutes to form a viscous brown precipitate on hydrolysis. After stirring at room temperature for 2 hours, toluene, ethoxyethanol and water were distilled off under reduced pressure to obtain a precursor of a LaFeCoPd composite oxide.

The precursor was placed on a petri dish, subjected to forced-air drying at 60° C. for 24 hours, and subjected to heat treatment at 800° C. in the atmosphere for one hour using an electric furnace to obtain a blackish brown powder.

Figure 2:
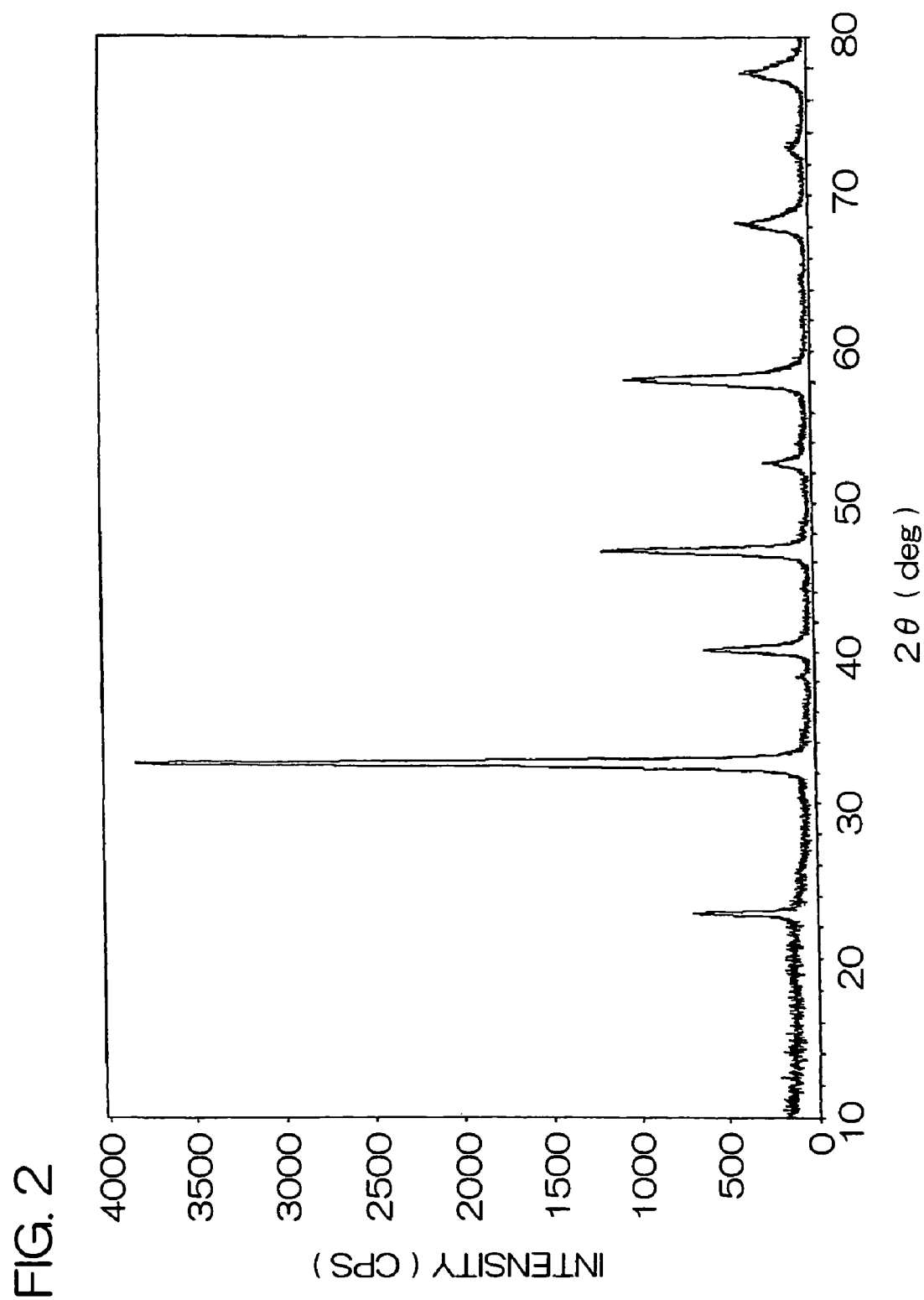
FIG. 2 is a graph showing an X-ray diffraction spectrum of a powder of Production Example 2.

An X-ray powder diffraction analysis of the powder was conducted. As a result, it was identified as a single crystal phase comprising a composite oxide having a perovskite-type structure of $La_{1.00}Fe_{0.57}Co_{0.38}Pd_{0.05}O_3$. The powder was found to have a specific surface area of 9.2 m$^2$/g and a Pd content in the composite oxide of 2.16% by mass. FIG. 2 is a graph showing this X-ray diffraction spectrum.

Production Example 3 (Production of $La_{1.00}Fe_{0.95}Pd_{0.05}O_3$)

| | |
|---|---|
| Lanthanum methoxypropylate | 40.7 g (0.100 mol) |
| Iron methoxypropylate | 30.7 g (0.095 mol) |

A mixed alkoxide solution was prepared by charging the above components in a 500 mL round-bottomed flask and dissolving them in 200 mL of toluene with stirring.

Separately, 1.52 g (0.005 mol) of palladium acetylacetonate was dissolved in 100 mL of toluene and the resulting solution was added to the mixed alkoxide solution to obtain a homogenous mixed solution containing LaFePd.

Then, a blackish brown powder was obtained by the same operation as in Production Example 2.

Figure 3:
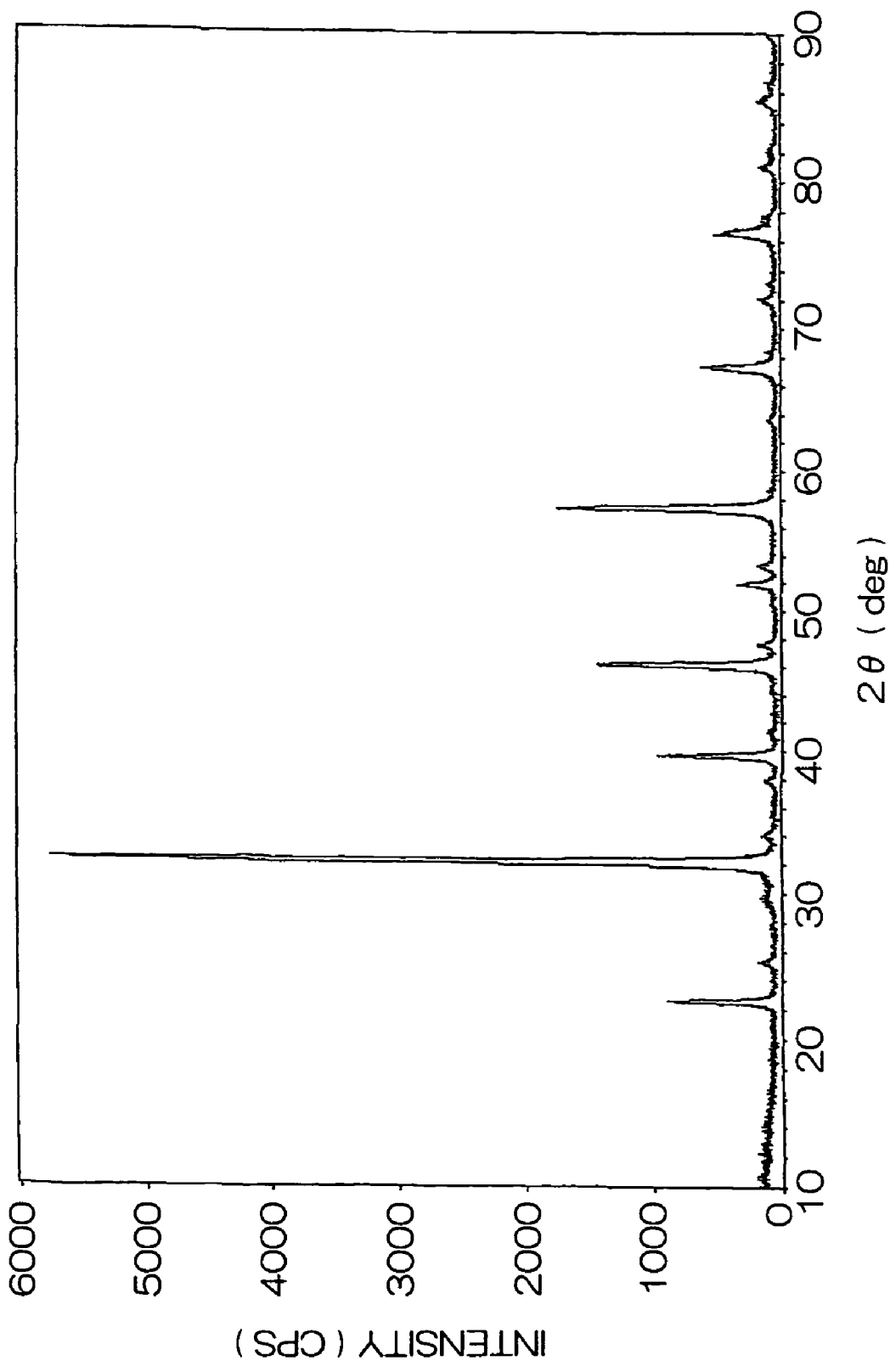
FIG. 3 is a graph showing an X-ray diffraction spectrum of a powder of Production Example 3.

An X-ray powder diffraction analysis of the powder was conducted. As a result, it was identified as a single crystal phase comprising a composite oxide having a perovskite-type structure of $La_{1.00}Fe_{0.95}Pd_{0.05}O_3$. The powder was found to have a specific surface area of 17 m$^2$/g and a Pd content in the composite oxide of 2.17% by mass. FIG. 3 is a graph showing this X-ray diffraction spectrum.

Production Example 4 (Production of $Pr_{0.90}Sr_{0.10}Mn_{0.90}Pd_{0.10}O_3$)

| | |
|---|---|
| Praseodymium methoxypropylate | 36.7 g (0.090 mol) |
| Strontium methoxypropylate | 2.7 g (0.010 mol) |
| Manganese methoxypropylate | 21.0 g (0.090 mol) |

A mixed alkoxide solution was prepared by charging the above components in a 500 mL round-bottomed flask and dissolving them in 200 mL of toluene with stirring.

Separately, 3.04 g (0.010 mol) of palladium acetylacetonate was dissolved in 100 mL of toluene and the resulting solution was added to the mixed alkoxide solution to obtain a homogenous mixed solution containing PrSrMnPd.

Then, a blackish brown powder was obtained by the same operation as in Production Example 2.

Figure 4:
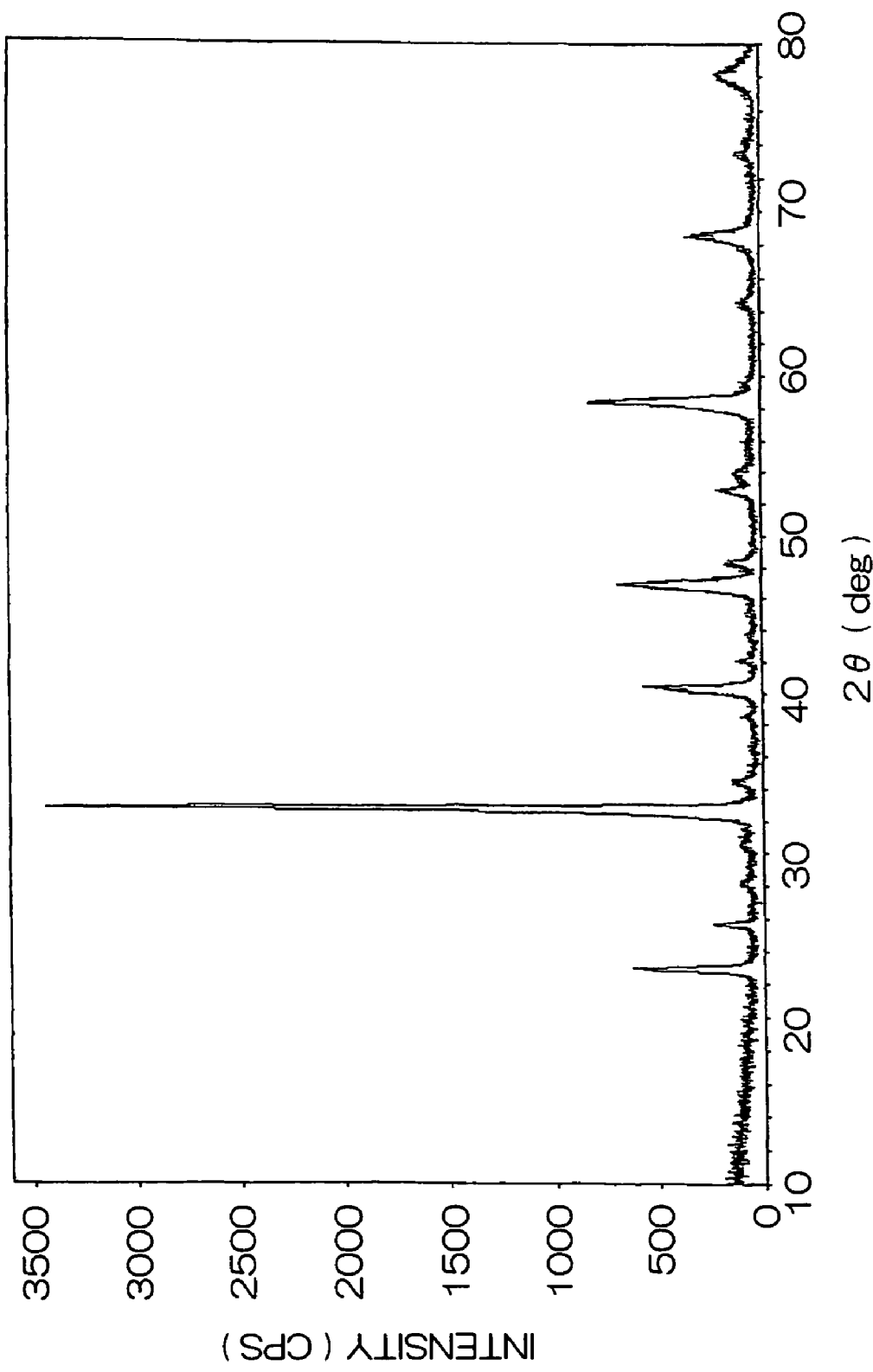
FIG. 4 is a graph showing an X-ray diffraction spectrum of a powder of Production Example 4.

An X-ray powder diffraction analysis of the powder was conducted. As a result, it was identified as a single crystal phase comprising a composite oxide having a perovskite-type structure of $Pr_{0.90}Sr_{0.10}Mn_{0.90}Pd_{0.10}O_3$. The powder was found to have a specific surface area of 0.5 m$^2$/g and a Pd content in the composite oxide of 4.37% by mass. FIG. 4 is a graph showing this X-ray diffraction spectrum.

Production Example 5 (Production of $Nd_{0.50}Y_{0.50}Fe_{0.57}Cu_{0.38}Pd_{0.05}O_3$)

| | |
|---|---|
| Neodymium ethoxyethylate | 20.6 g (0.050 mol) |
| Yttrium ethoxyethylate | 17.8 g (0.050 mol) |
| Iron ethoxyethylate | 18.4 g (0.057 mol) |
| Copper ethoxyethylate | 9.2 g (0.038 mol) |

A mixed alkoxide solution was prepared by charging the above components in a 500 mL round-bottomed flask and dissolving them in 200 mL of toluene with stirring.

Separately, 1.52 g (0.005 mol) of palladium acetylacetonate was dissolved in 100 mL of toluene and the resulting solution was added to the mixed alkoxide solution to obtain a homogenous mixed solution containing NdYFeCuPd.

Then, a blackish brown powder was obtained by the same operation as in Production Example 2.

Figure 5:
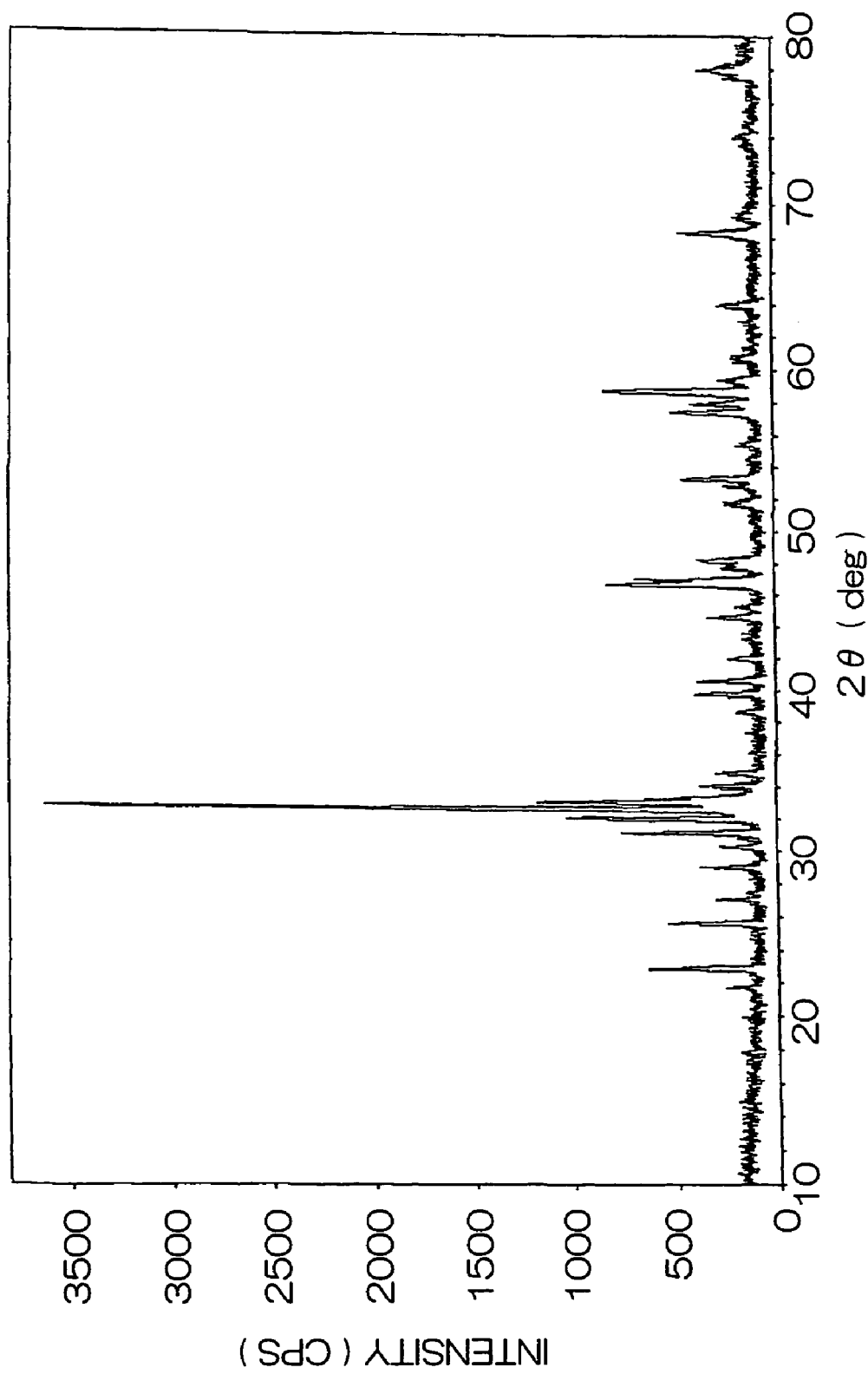
FIG. 5 is a graph showing an X-ray diffraction spectrum of a powder of Production Example 5.

An X-ray powder diffraction analysis of the powder revealed that it was identified as a composite oxide in which a perovskite-type structure of $Nd_{0.50}Y_{0.50}Fe_{0.57}Cu_{0.38}Pd_{0.05}O_3$ is a control phase. The powder was found to have a specific surface area of 4.2 m$^2$/g and a Pd content in the composite oxide of 2.36% by mass. FIG. 5 is a graph showing this X-ray diffraction spectrum.

2) Synthesis Examples by Sonogashira Reaction 2-1) Reaction of Aryl Iodide and Phenylacetylene Synthesis Example 1 (Production of 1-chloro-4-(phenylethynyl)benzene)

| | |
|---|---|
| 4-chloroiodobenzene | 2.38 g (0.010 mol) |
| Phenylacetylene | 1.13 g (0.011 mol) |
| Triethylamine | 4.06 g (0.040 mol) |

A solution was prepared by charging the above components in a 100 mL round-bottomed flask equipped with a stirrer, a thermometer and a reflux condenser, the atmosphere of which is replaced by nitrogen, and dissolving them in 40 mL of measured DMF/deionized water (1:1).

To the resulting solution, 62.1 mg (0.25 mmol, equivalent to 2.5 mol %) of $La_{1.00}Fe_{0.57}Cu_{0.38}Pd_{0.05}O_3$ obtained in Production Example 1 was added as a catalyst for synthesis reaction followed by heating using a mantle heater and further heating under reflux at 100° C. for 24 hours. After the completion of the reaction, 100 mL of toluene and 50 mL of an aqueous 5% NaCl solution were added and an organic layer was separated and further washed with 50 mL of deionized water. To the organic layer, 10 g of sodium sulfate was added, followed by well shaking, drying, filtrating, and washing with toluene. Then, the solvent was distilled off from the resulting filtrate.

The residue was purified by silica gel column chromatography using n-hexane/ethyl acetate (50:1) as an eluent to obtain 1.66 g of a white crystal. The white crystal was found to have a melting point of 83 to 84° C. and a yield of 78.0% in terms of 4-chloroiodobenzene.

Results of elemental analysis are as shown below. A theoretical value is shown in parentheses.
C: 75.23% (75.66%)
H: 4.13% (4.09%)

Synthesis Example 2 (Production of 1-chloro-4-(phenylethynyl)benzene)

| 4-chloroiodobenzene | 59.6 mg (0.25 mmol) |
| Phenylacetylene | 56.2 mg (0.55 mmol) |
| Sodium carbonate | 53.1 mg (0.50 mmol) |
| Tetra-n-butylammonium bromide | 80.6 mg (0.25 mmol) |

A solution was prepared by charging the above components in a 5 mL ampule tube, the atmosphere of which is replaced by nitrogen, and dissolving them in 2 mL of measured deionized water.

To the resulting solution, 1.55 mg (0.0063 mmol, equivalent to 2.5 mol %) of $La_{1.00}Fe_{0.57}Cu_{0.38}Pd_{0.05}O_3$ obtained in Production Example 1 was added as a catalyst for synthesis reaction followed by sealing the tube and further heating using microwave at 175° C. for 20 minutes.

After cooling to room temperature, the reaction product was dissolved in 20 mL of toluene and separated, and then the organic layer was washed with 10 mL of an aqueous 5% NaCl solution. To the organic layer, 2 g of sodium sulfate was added, followed by well shaking, drying, filtrating, and washing with toluene. Then, the solvent was distilled off from the resulting filtrate.

The residue was purified by silica gel column chromatography using n-hexane/ethyl acetate (50:1) as an eluent to obtain 40.0 mg of a white crystal. The white crystal was found to have a melting point of 83 to 84° C. and a yield of 75.2% in terms of 4-chloroiodobenzene.

Results of elemental analysis are as shown below. A theoretical value is shown in parentheses.
C: 75.87% (75.66%)
H: 4.04% (4.09%)

Synthesis Example 3 (Production of 1,2-diphenylacetylene)

| Iodobenzene | 2.04 g (0.010 mol) |
| Phenylacetylene | 2.25 g (0.022 mol) |
| Sodium carbonate | 3.18 g (0.030 mol) |
| Tetra-n-butylammonium bromide | 3.22 g (0.010 mol) |

A solution was prepared by charging the above components in a 100 mL round-bottomed flask equipped with a stirrer, a thermometer and a reflux condenser, the atmosphere of which is replaced by nitrogen, and dissolving them in 15 mL of toluene and 15 mL of measured deionized water.

To the solution, 124.1 mg (0.5 mmol, equivalent to 5 mol %) of $La_{1.00}Fe_{0.57}Cu_{0.38}Pd_{0.05}O_3$ obtained in Production Example 1 was added as a catalyst for synthesis reaction followed by heating using a mantle heater and further heating under reflux at 90° C. for 5 hours. After the completion of the reaction, 50 mL of toluene was added, and the organic layer was separated and washed with 30 mL of an aqueous 5% NaCl solution. To the organic layer, 10 g of sodium sulfate was added, followed by well shaking, drying, filtrating and washing with toluene. Then, the solvent was distilled off from the resulting filtrate.

The obtained residue was purified by silica gel column chromatography using n-hexane as an eluent to obtain 1.60 g of a white crystal. The white crystal was found to have a melting point of 59 to 61° C. and a yield of 89.8% in terms of iodobenzene.

Results of elemental analysis are as shown below. A theoretical value is shown in parentheses.
C: 94.17% (94.33%)
H: 5.83% (5.67%)

2-2) Reaction of Arylbromide and 4-ethynylanisole

Synthesis Example 4 (Production of 1-nitro-4-[(4-methoxyphenyl)ethynyl]benzene)

| p-bromonitrobenzene | 2.02 g (0.010 mol) |
| 4-ethynylanisole | 2.25 g (0.011 mol) |
| Triethylamine | 4.04 g (0.040 mol) |

A solution was prepared by charging the above components in a 100 mL round-bottomed flask equipped with a stirrer, a thermometer and a reflux condenser, the atmosphere of which is replaced by nitrogen, and dissolving them in 35 mL of measured DMAC/deionized water (95:5).

To the solution, 62.1 mg (0.25 mmol, equivalent to 2.5 mol %) of $La_{1.00}Fe_{0.57}Cu_{0.38}Pd_{0.05}O_3$ obtained in Production Example 1 was added as a catalyst for synthesis reaction followed by heating using a mantle heater and heating under reflux at 120° C. for 12 hours. After the completion of the reaction, 150 mL of toluene and 100 mL of an aqueous 5% NaCl solution were added, and the organic layer was separated and further washed with 100 mL of deionized water. To the organic layer, 10 g of sodium sulfate was added, followed by well shaking, drying, filtrating and washing with toluene. Then, the solvent was distilled off from the resulting filtrate.

The obtained residue was purified by silica gel column chromatography using n-hexane/ethyl acetate (50:1) as an eluent to obtain 1.81 g of a white crystal. The white crystal was found to have a melting point of 118 to 120° C. and a yield of 71.2% in terms of p-bromonitrobenzene.

Results of elemental analysis are as shown below. Theoretical values are shown in parentheses.
C: 70.89% (71.13%)
H: 4.30% (4.39%)
O: 19.03% (18.95%)

2-3) Reaction of Iodothiophene and Phenylacetylene

Synthesis Example 5 (Production of 2-(phenylethynyl)thiophene)

| 2-iodothiophene | 2.10 g (0.010 mol) |
| Phenylacetylene | 2.25 g (0.022 mol) |
| Sodium carbonate | 3.18 g (0.030 mol) |
| Tetra-n-butylammonium bromide | 3.22 g (0.010 mol) |

A solution was prepared by charging the above components in a 100 mL round-bottomed flask equipped with a stirrer, a thermometer and a reflux condenser, the atmosphere of which is replaced by nitrogen, and dissolving them in 15 mL of toluene and 15 mL of measured deionized water.

To the solution, 124.1 mg (0.5 mmol, equivalent to 5 mol %) of $La_{1.00}Fe_{0.57}Cu_{0.38}Pd_{0.05}O_3$ obtained in Production Example 1 was added as a catalyst for synthesis reaction followed by heating using a mantle heater and heating under reflux at 90° C. for 7 hours. After the completion of the reaction, 50 mL of toluene was added, the solution was separated and the organic layer was washed with 30 mL of an aqueous 5% NaCl solution. To the organic layer, 10 g of sodium sulfate was added, followed by well shaking and drying, filtrating and washing with toluene. Then, the solvent was distilled off from the resulting filtrate.

The obtained residue was purified by silica gel column chromatography using n-hexane as an eluent to obtain 1.51 g of a white crystal. The white crystal was found to have a melting point of 51 to 52° C. and a yield of 82.1% in terms of 2-iodothiophene.

Results of elemental analysis are as shown below. Theoretical values are shown in parentheses.
C: 78.38% (78.21%)
H: 4.40% (4.38%)

2-4) Reaction of Iodobenzene and Trimethylsilylacetylene

Synthesis Example 6 (Production of 1-phenyl-2-(trimethylsilyl)acetylene)

| Iodobenzene | 0.51 g (2.5 mmol) |
| Trimethylsilylacetylene | 0.54 g (5.5 mol) |
| Piperidine | 0.85 g (10.0 mmol) |

The above components were charged in a 5 mL ampule tube, the atmosphere of which was replaced by nitrogen.

To the resulting mixture, 31.0 mg (0.125 mmol, equivalent to 5 mol %) of $La_{1.00}Fe_{0.57}Cu_{0.38}Pd_{0.05}O_3$ obtained in Production Example 1 was added as a catalyst for synthesis reaction and the ampule tube was equipped with a magnetic stirrer, followed by sealing and heating with stirring using an oil bath at 170° C. for 2 hours.

After cooling to room temperature, the obtained reaction product was dissolved in 20 mL of toluene and separated, and then an organic layer was washed with 10 mL of an aqueous 5% NaCl solution. To the organic layer, 2 g of sodium sulfate was added, followed by well shaking, drying, filtrating and washing with toluene. Then, the solvent was distilled off from the resulting filtrate.

The obtained residue was purified by silica gel column chromatography using n-hexane as an eluent to obtain 0.21 g of a colorless liquid. The colorless liquid was found to have a boiling point of 87 to 88° C./9 mmHg and a yield of 48.0% in terms of iodobenzene.

The results of elemental analysis are as shown below. Theoretical values are shown in parentheses.
C: 75.88% (75.78%)
H: 8.05% (8.11%)

2-5) Reaction of Iodoacetophenone and Phenylacetylene

Synthesis Example 7 (Production of 4-(phenylethynyl)acetophenone)

| p-iodoacetophenone | 2.46 g (0.010 mol) |
| Phenylacetylene | 1.12 g (0.011 mol) |
| Triethylamine | 4.04 g (0.040 mol) |

A solution was prepared by charging the above components in a 100 mL round-bottomed flask equipped with a stirrer, a thermometer and a reflux condenser, the atmosphere of which is replaced by nitrogen, and dissolving them in 40 mL of measured DMF/deionized water (95:5).

To the solution, 61.6 mg (0.25 mmol, equivalent to 2.5 mol %) of $La_{1.00}Fe_{0.57}Co_{0.38}Pd_{0.05}O_3$ obtained in Production Example 2 was added as a catalyst for synthesis reaction followed by heating using a mantle heater and further heating under reflux at 120° C. for 24 hours. After the completion of the reaction, 150 mL of toluene and 100 mL of an aqueous 5% NaCl solution were added, and the organic layer was separated and further washed with 100 mL of deionized water. To the organic layer, 10 g of sodium sulfate was added, followed by well shaking, drying, filtrating and washing with toluene. Then, the solvent was distilled off from the resulting filtrate.

The obtained residue was purified by silica gel column chromatography using n-hexane/ethyl acetate (20:1) as an eluent to obtain 1.54 g of a white crystal. The white crystal was found to have a melting point of 96 to 98° C. and a yield of 70.0% in terms of p-iodoacetophenone.

Results of elemental analysis are as shown below. Theoretical values are shown in parentheses.
C: 87.55% (87.23%)
H: 5.43% (5.50%)
O: 7.34% (7.26%)

The same reaction as in Synthesis Example 7 was conducted under the same conditions using different catalysts (Production Examples 1 and 3 to 5). The results are shown in Table 1.

TABLE 1

| Catalyst | Composition | Amount (mol %) | Yield (%) |
|---|---|---|---|
| Production Example 1 | $La_{1.0}Fe_{0.57}Cu_{0.38}Pd_{0.05}O_3$ | 62.0 mg (2.5 mol %) | 68.1 |
| Production Example 3 | $La_{1.0}Fe_{0.95}Pd_{0.05}O_3$ | 61.3 mg (2.5 mol %) | 78.5 |
| Production Example 4 | $Pr_{0.9}Sr_{0.10}Mn_{0.90}Pd_{0.10}O_3$ | 30.5 mg (1.25 mol %) | 66.7 |
| Production Example 5 | $Nd_{0.5}Y_{0.5}Fe_{0.57}Cu_{0.38}Pd_{0.05}O_3$ | 56.5 mg (2.5 mol %) | 58.9 |

While the illustrative embodiments and examples of the present invention are provided in the above description, such is for illustrative purpose only and it is not to be construed restrictively. Modification and variation of the present invention which will be obvious to those skilled in the art is to be covered in the following claims.

INDUSTRIAL APPLICABILITY

The method for synthesizing a compound of the present invention is fit for various uses where the Sonogashira reaction is industriously used, for example, synthesis of drug intermediates, synthetic polymer materials, liquid crystal materials and optical materials.

The invention claimed is:

1. A method for synthesizing a compound, comprising:
reacting a compound represented by the following formula (1) with a compound represented by the following general formula (2) in a presence of a perovskite-type composite oxide containing palladium:

$$R_1\text{—}X \quad (1)$$

wherein $R_1$ represents an aryl group which may have a substituent, a heterocyclic group which may have a substituent or an alkenyl group which may have a substituent, and X represents a halogen atom excluding fluorine, a trifluoromethanesulfonyloxy group, and $$HC\equiv CR_2 \quad (2)$$

wherein $R_2$ represents a hydrogen atom, an aryl group which may have a substituent, a heterocyclic group which may have a substituent, and alkyl group which may have a substituent, an alkenyl group which may have a substituent or trialkyl-substituted silyl group.

2. The method for synthesizing a compound according to claim 1, wherein the perovskite-type composite oxide containing palladium is represented by the following formula (3):

$$AB_{1-z}Pd_zO_3 \quad (3)$$

wherein A represents at least one element selected from rare-earth elements and alkaline earth metals, B represents at least one element selected from transition elements excluding rare-earth elements and Pd, and Al, and z represents an atomic ratio of Pd.

3. The method for synthesizing a compound according to claim 1, wherein the perovskite-type composite oxide containing palladium is represented by the following formula (4):

$$A_{1-x}A'_xB_{1-(y+z)}Cu_yPd_zO_3 \quad (4)$$

wherein A represents at least one element selected from rare-earth elements, A' represents at least one element selected from alkaline earth metals, B represents at least one element selected from transition elements excluding rare-earth elements, Cu and Pd, and Al, x represents an atomic ratio satisfying the following relation: $0\leq x\leq 0.5$, y represents an atomic ratio satisfying the following relation: $0<y\leq 0.5$, and z represents an atomic ratio satisfying the following relation: $0<z\leq 0.5$.

4. The method for synthesizing a compound according to claim 1, wherein the perovskite-type composite oxide containing palladium is represented by the following formula (5):

$$AB_{1-(y+z)}Cu_yPd_zO_3 \quad (5)$$

wherein A represents at least one element selected from Y, La, Ce, Pr and Nd, B represents at least one element selected from Mn, Fe, Co and Al, y represents an atomic ratio satisfying the following relation: $0<y\leq 0.5$, and z represents an atomic ratio satisfying the following relation: $0<z\leq 0.5$.

* * * * *